(12) United States Patent
Vayser et al.

(10) Patent No.: US 9,011,323 B2
(45) Date of Patent: Apr. 21, 2015

(54) METHOD AND APPARATUS FOR SOFT TISSUE RETRACTION

(75) Inventors: Alex Vayser, Mission Viejo, CA (US); Edward A. Covey, Mission Viejo, CA (US); James K. Bredenkamp, Mission Viejo, CA (US); Leland A. Stock, San Diego, CA (US)

(73) Assignee: Invuity, Inc., San Francisco, CA (US)

( * ) Notice: Subject to any disclaimer, the term of this patent is extended or adjusted under 35 U.S.C. 154(b) by 167 days.

(21) Appl. No.: 13/253,785

(22) Filed: Oct. 5, 2011

(65) Prior Publication Data

US 2012/0116170 A1    May 10, 2012

Related U.S. Application Data

(60) Provisional application No. 61/391,512, filed on Oct. 8, 2010.

(51) Int. Cl.
| | |
|---|---|
| *A61B 1/32* | (2006.01) |
| *A61B 1/06* | (2006.01) |
| *A61B 17/02* | (2006.01) |
| *A61B 19/00* | (2006.01) |

(52) U.S. Cl.
CPC .............. *A61B 1/32* (2013.01); *A61B 1/0676* (2013.01); *A61B 17/02* (2013.01); *A61B 19/5202* (2013.01)

(58) Field of Classification Search
USPC .................................................. 600/184–235
See application file for complete search history.

(56) References Cited

U.S. PATENT DOCUMENTS

| | | | |
|---|---|---|---|
| 3,638,644 A * | 2/1972 | Reick | 600/191 |
| 3,641,332 A | 2/1972 | Reick et al. | |
| 3,890,960 A | 6/1975 | Wunsch et al. | |
| 4,226,228 A | 10/1980 | Shin et al. | |
| 4,562,832 A | 1/1986 | Wilder et al. | |
| 4,592,344 A | 6/1986 | Scheer | |
| 4,597,030 A | 6/1986 | Brody et al. | |
| 4,605,990 A | 8/1986 | Wilder et al. | |
| 4,643,172 A | 2/1987 | Taff et al. | |
| 4,697,578 A | 10/1987 | Burgin | |
| 4,807,599 A | 2/1989 | Robinson et al. | |
| 4,842,356 A | 6/1989 | Mori | |
| 4,961,617 A | 10/1990 | Shahidi et al. | |

(Continued)

FOREIGN PATENT DOCUMENTS

| | | |
|---|---|---|
| EP | 0101781 A1 | 3/1984 |
| GB | 2078526 A | 1/1982 |

*Primary Examiner* — Eduardo C Robert
*Assistant Examiner* — Steven Cotroneo
(74) *Attorney, Agent, or Firm* — Wilson Sonsini Goodrich & Rosati

(57) ABSTRACT

A soft tissue retractor includes a retractor body and a proximal projection extends generally perpendicular to the proximal end of the retractor body. An illumination waveguide engages a slot in the retractor blade to provide illumination to a surgical site while maintaining total internal reflection in the waveguide. An illumination input is formed into the proximal end of the illumination waveguide for conducting light from a source to the illumination waveguide. The proximal projection is configured for application of counter traction without the need for squeezing the retractor body. The proximal projection may be weighted to balance the soft tissue retractor as well as enabling the retractor to provide counter traction by itself. The configuration of the proximal projection further enables self-retraction by including a flat foot to prevent rolling and sliding of the retractor when it is providing self-retraction.

8 Claims, 4 Drawing Sheets

(56) References Cited

U.S. PATENT DOCUMENTS

| | | |
|---|---|---|
| 5,035,232 A | 7/1991 | Lutze et al. |
| 5,353,786 A | 10/1994 | Wilk |
| 5,938,591 A * | 8/1999 | Minson .................. 600/191 |
| 6,185,356 B1 | 2/2001 | Parker et al. |
| 6,504,985 B2 | 1/2003 | Parker et al. |
| 6,743,424 B1 * | 6/2004 | Donovan .................. 424/94.5 |
| 7,306,559 B2 * | 12/2007 | Williams .................. 600/245 |
| 2002/0010388 A1 * | 1/2002 | Taylor et al. .................. 600/204 |
| 2008/0002426 A1 * | 1/2008 | Vayser et al. .................. 362/574 |
| 2010/0249639 A1 * | 9/2010 | Bhatt .................. 600/546 |

* cited by examiner

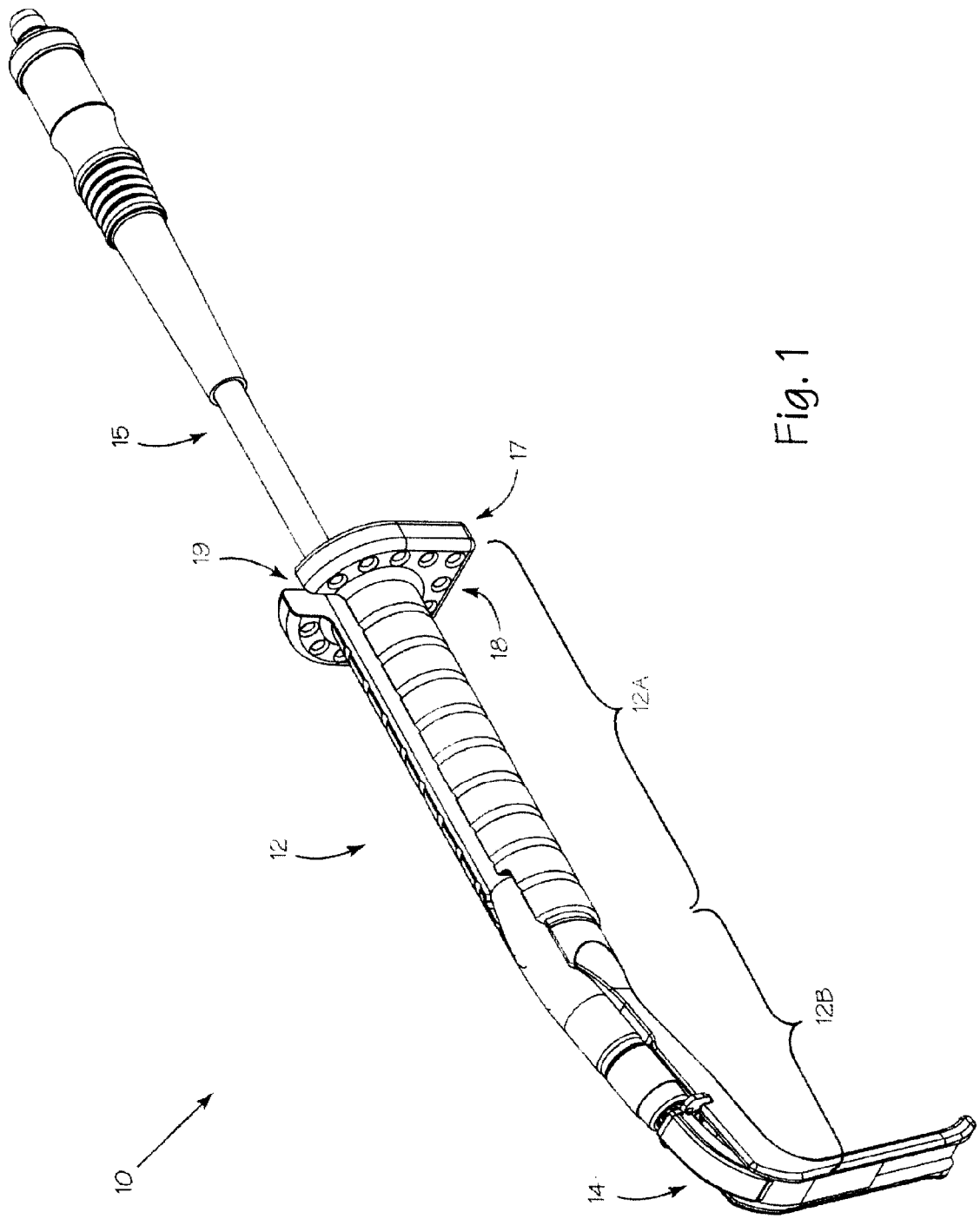

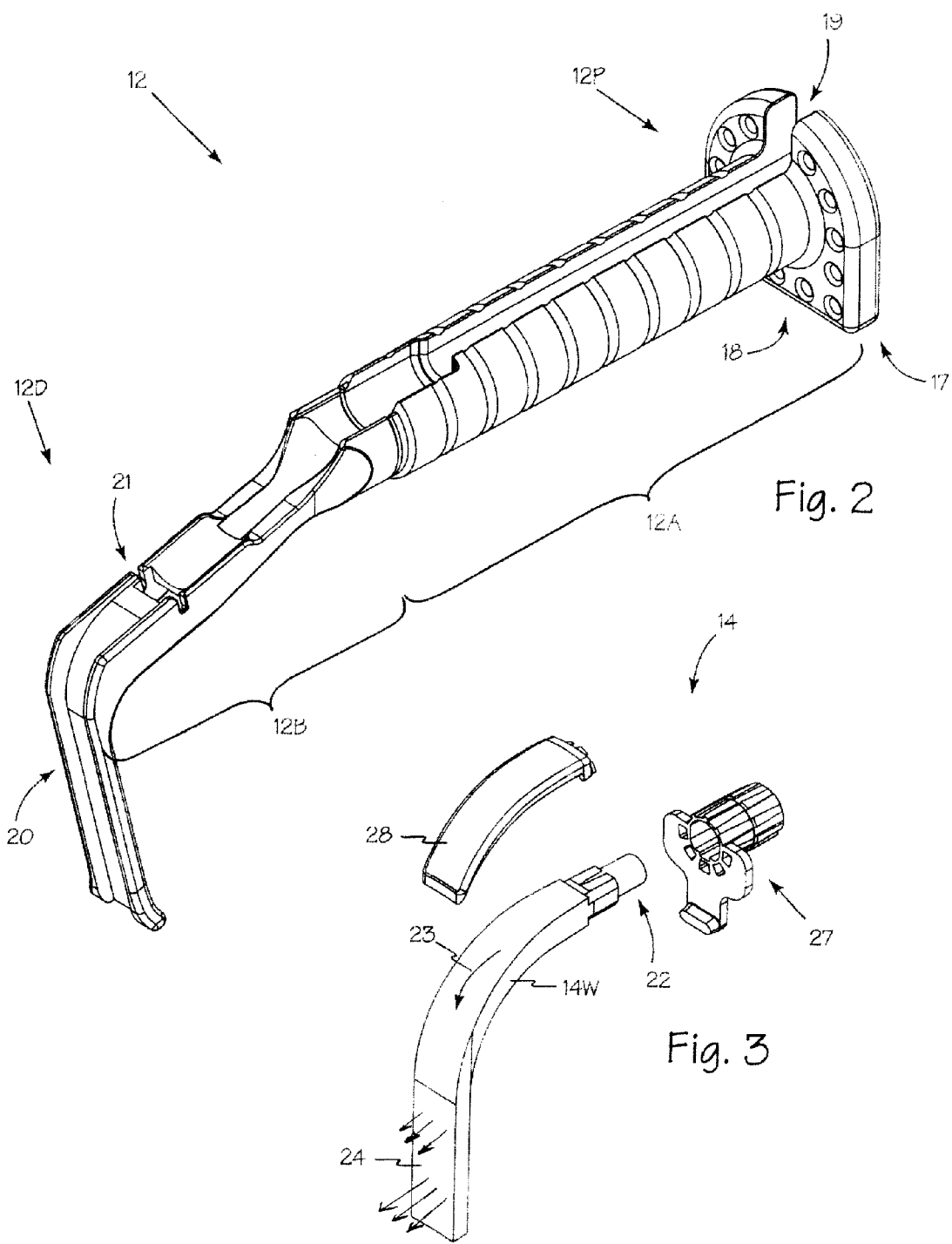

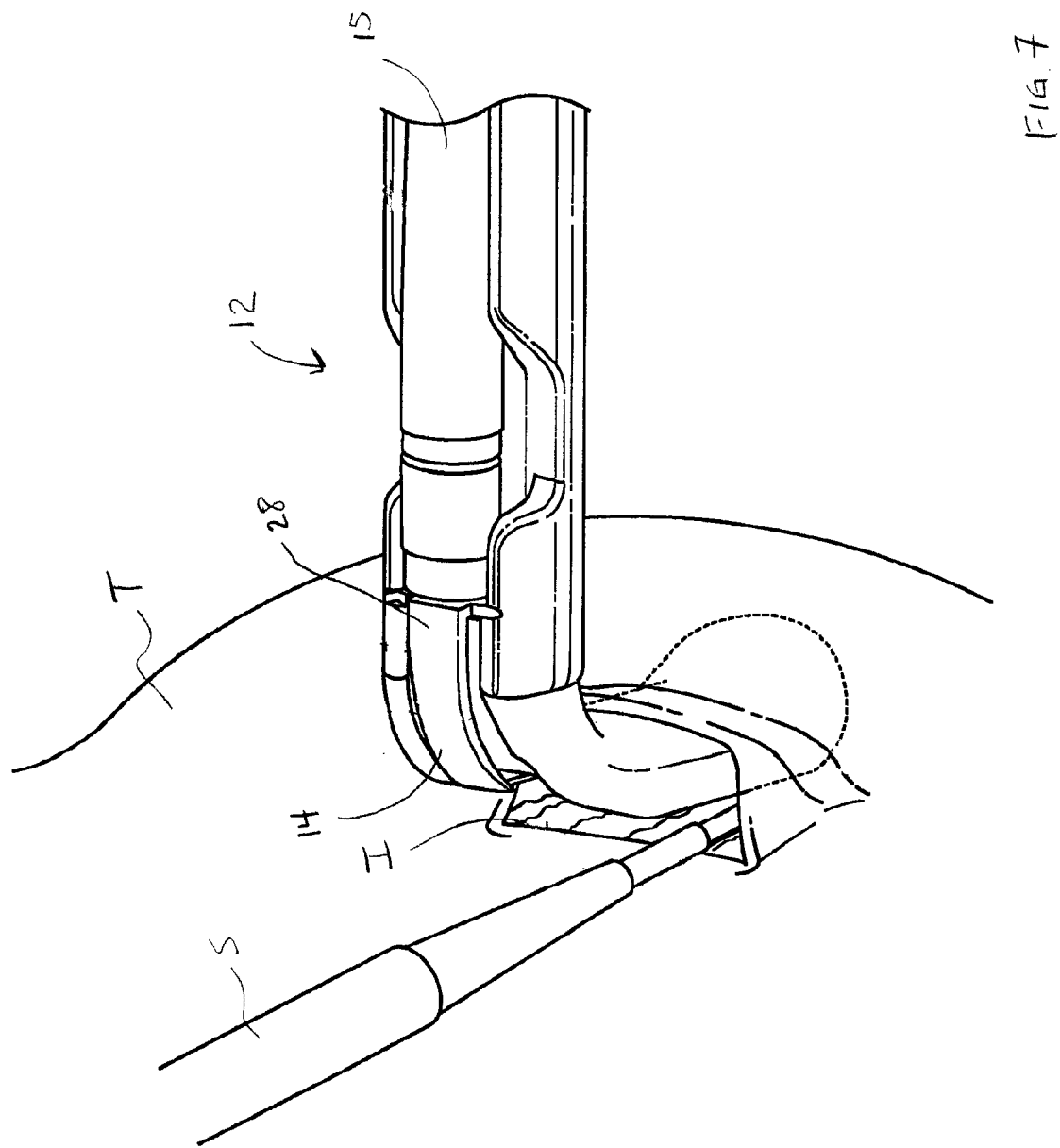

METHOD AND APPARATUS FOR SOFT TISSUE RETRACTION

CROSS-REFERENCE

The present application is a non-provisional of, and claims the benefit of U.S. Provisional Patent Application No. 61/391,512 filed Oct. 8, 2010; the entire contents of which is incorporated herein by reference.

BACKGROUND OF THE INVENTION

The present invention relates generally to the field of soft tissue retraction for minimally invasive surgery and more specifically to methods and illumination systems with integrated retractors for minimally invasive soft tissue retraction.

In various surgical procedures, illumination of the surgical field is typically achieved through the use of overhead lighting, headlamps and surgical microscopes. There are scenarios in which these illumination sources provide lighting that is either poor in quality or poorly directed. Light from an overhead source is fixed and often blocked by the surgeon or others in the operating room. Surgical microscopes are little better and headlamps may be adjusted as a physician tilts or moves his head to redirect the output beam, but still may be blocked by various anatomical structures or layers of tissue and muscle. Lighting from either source may not be adequate as the physician progresses through various phases of the procedure requiring visualization of the anatomy at varied depths from the skin-level incision. Additionally some illuminated surgical systems are not efficient at transmitting light and therefore require a powerful light source which can generate excessive amounts of heat that may be uncomfortable for a surgeon or others in the operating room.

Conventional retractors are often not suitable for minimally invasive procedures. The incisions are often too small and the resulting surgical site too deep for conventional retractors. Also, some conventional retractors are not always ergonomically designed to be comfortable for an operator to retract various tissue from different positions.

Thus, it would be desirable to provide improved surgical retractors which can illuminate the surgical field more effectively. It would also be desirable to provide improved surgical retractors that are more comfortable for a surgeon and that can accommodate various anatomies and surgical fields better than existing instruments. At least some of these objectives will be met by the embodiments disclosed herein.

SUMMARY OF INVENTION

The devices described below provide improved illumination for minimally invasive surgery and may include a retractor body with an improved retractor blade suitable for minimally invasive surgery. This illuminated retractor is useful in a wide array of surgical procedures performed in deep, restricted and/or awkward surgical fields including open and minimally invasive procedures.

An illuminated soft tissue retractor may include a retractor body having a proximal end and a distal end, the proximal end having a proximal projection extending generally perpendicular to the retractor body, the distal end including a slotted retractor blade. An illumination waveguide engages the retractor blade slot to provide illumination to a surgical site surrounding the retractor blade while maintaining total internal reflection. An illumination input is formed into the proximal end of the illumination waveguide for conducting light from a source to the illumination waveguide.

The proximal projection may be configured for application of counter traction without the need for squeezing the retractor body which often leads to operator fatigue. The proximal projection may be weighted to balance the instrument as well as enabling the retractor to provide counter traction by itself. The configuration of the proximal projection further enables self-retraction by including a generally flat foot to prevent rolling and sliding of the retractor when it is providing self-retraction.

In a first aspect of the present invention, an illuminated soft tissue retractor comprises a retractor body having a proximal end and a distal end, an illumination waveguide, and an illumination input. The proximal end of the retractor body has a proximal projection extending generally perpendicular to the retractor body, and the distal end of the retractor body includes a retractor blade. The illumination waveguide has a proximal end and a distal end, and the illumination waveguide engages the retractor blade to provide illumination to a surgical site surrounding the retractor blade. The illumination waveguide is configured to conduct light from the proximal end to the distal end by total internal reflection. The illumination input is formed into the proximal end of the illumination waveguide for conducting light from a source to the illumination waveguide.

The retractor body may include a source of illumination and a portable source of energy to generate illumination. The proximal projection may be weighted to control the center of mass of the illuminated soft tissue retractor. The illumination waveguide may comprise a light input and a collar disposed thereover such that an air gap is maintained around the light input. The light input may have a generally cylindrical proximal portion transitioning into a rectangular distal portion, and the distal portion may be optically coupled with the illumination waveguide. The retractor may further comprise a shield that is disposed over the illumination waveguide which protects the illumination waveguide from damage caused by other surgical instruments. The shield may also prevent glare from shining back into a surgeon's eyes. The retractor blade may comprise a substantially rectangular portion and a flared distal tip. The retractor blade may form a drop angle with the retractor body, and the drop angle may range from 5 to 35 degrees. The retractor may further comprise a flat foot disposed on the proximal projection which facilitates self-retraction by preventing rolling and sliding of the retractor.

In another aspect of the present invention, a method of performing a minimally invasive thyroidectomy on a patient comprises providing an illuminated soft tissue retractor having a retractor blade, creating a minimally invasive surgical incision, and inserting the retractor blade into the incision. The soft tissue retractor also has a retractor body and an illumination waveguide. The retractor blade is coupled to the retractor body and the illumination waveguide is coupled to the retractor blade. The incision is preferably within 1 cm of the cricoids cartilage of the patient. The method also includes illuminating the surgical field with light extracted from the illumination waveguide. The light is directed laterally and distally from the illumination waveguide to illuminate the surgical field, and the light is transmitted through the illumination waveguide by total internal reflection. The soft tissue retractor retracts tissue thereby permitting a surgeon to perform a thyroidectomy or other procedure. The thyroidectomy may comprise using the soft tissue retractor to expose and dissect the patient's thyroid. The retractor blade may be used to bluntly dissect tissue, or the retractor blade may also be used to counter retract tissue. Counter retracting tissue may comprise providing a proximal projection disposed adjacent a proximal end of the retractor body such that the counter retraction may be applied without squeezing the retractor body. Creating the minimally invasive surgical incision may comprise making an incision no longer than 3 to 4 cm long. The method may also comprise protecting the waveguide illuminator by providing a shield that is disposed adjacent the waveguide illuminator. The shield may also block glare by preventing the glare from shining back into an operator's eyes.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a perspective view of an illuminated soft tissue retractor.

FIG. 2 is a perspective view of the illuminated soft tissue retractor seen in FIG. 1.

FIG. 3 is an exploded perspective view of the illuminated soft tissue retractor of FIG. 1.

FIG. 7 illustrates use of the retractor in FIG. 1 to retract tissue.

DETAILED DESCRIPTION OF THE INVENTION

Figure 4:
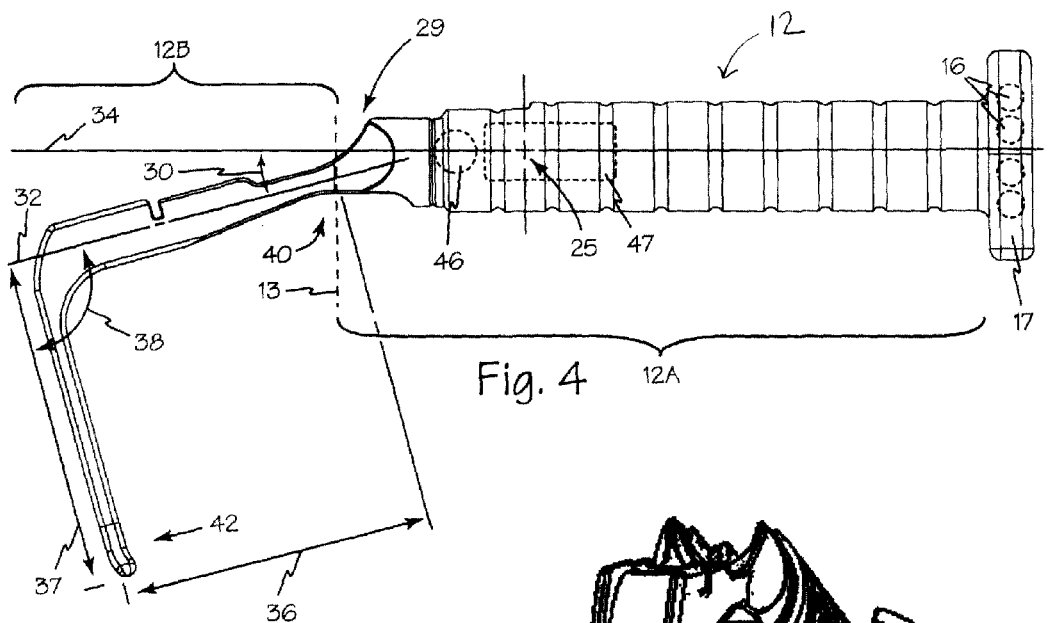
FIG. 4 is a side view of the illuminated soft tissue retractor of FIG. 1.

Referring to FIG. 1, illuminated soft tissue retractor 10 includes retractor assembly 12, illumination waveguide assembly 14 and illumination assembly 15. Proximal projection 17 extends generally perpendicular from retractor body 12A. Retractor blade 12B is coupled with a distal portion of the retractor body 12A and may include a proximal portion that is generally lies in the same plane as the retractor body 12A, and a distal portion which is transverse thereto. In some embodiments, the distal portion of the retractor blade is orthogonal to the proximal portion of the retractor blade, although other angles may be used. Proximal projection 17 optimizes application of counter traction without the need for squeezing retractor body 12A which often leads to fatigue. Proximal projection 17 may be weighted to balance the instrument as well as enabling the retractor to provide counter traction by itself. Proximal projection 17 may be formed of heavier material than retractor body 12A or retractor blade 12B. Alternatively, one or more weights may be secured within proximal projection 17 such as weights 16 (best seen in FIG. 4) to control the location of center of mass 25 as shown in FIG. 4. The weights 16 maybe releasably connected to the proximal projection 17 by disposing the weights in a plurality of apertures. The weights may be threadably engaged, press fit, or otherwise coupled with the proximal projection. The apertures may also be machined or otherwise formed into the proximal projection for proper weighting of the assembly.

The configuration of proximal projection 17 further enables self-retraction by including a generally flat foot or surface 18 to prevent rolling and sliding of the retractor when it is providing self-retraction. Retractor body 12A includes channel 19 to accommodate and engage illumination assembly 15 within the general profile of retractor body 12A. The illumination assembly 15 preferably includes a cable for optically coupling the waveguide assembly 14 with a light source (not illustrated). A proximal end of the illumination assembly 15 optically may include a standard optical connector such as an ACMI connector for coupling the cable with the light source.

Referring now to FIG. 2, retractor assembly 12 has a distal end 12D and a proximal end 12P. Proximal end 12P includes proximal projection 17, and distal end 12D includes retractor blade 12B. Retractor blade 12B includes waveguide socket 20 for engaging illumination waveguide assembly 14. One of more additional waveguide securing elements may also be included such as clip socket 21 for further engaging illumination waveguide assembly 14 and maintaining total internal reflection (TIR) of the light conducted through the waveguide by minimizing contact between retractor blade 12B and waveguide assembly 14. When contact between retractor blade 12B and waveguide assembly 14 cannot be eliminated, transmission efficiency is maintained by controlling where contact is made and minimizing the possibility of light escaping at the point(s) of contact. The waveguide may have active zones where light is transmitted through the waveguide by total internal reflection, and dead zones where substantially no light is transmitted by total internal reflection. Contact between the waveguide and the retractor blade is preferably limited to the dead zones of the waveguide in order to minimize light loss. Additionally, in preferred embodiments, an air gap is maintained between the active zones of the waveguide and the retractor blade, again to minimize light loss.

Figure 6:
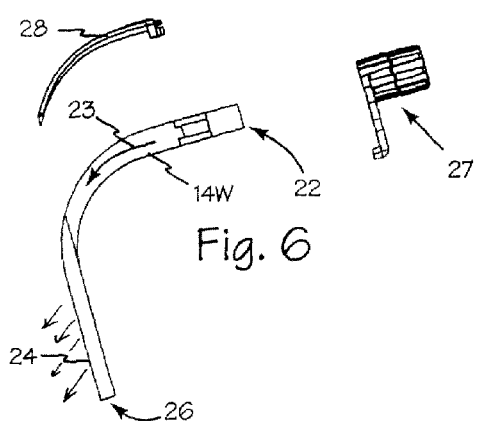
FIG. 6 is an exploded side view of the illumination waveguide assembly of FIG. 3.

Referring now to FIG. 3, waveguide assembly 14 includes waveguide 14W which is configured to provide optimal light conduction using total internal reflection (TIR) of the incident light introduced through light input 22. Light input 22 preferably has a round or cylindrical input transitioning into a square or rectangular section that is then coupled with the remainder of the waveguide. This transition zone creates dead zones in the square or rectangular portion of the light input 22 where substantially no light is transmitted by TIR, and thus this portion of the waveguide may be coupled to the clip 27 in order to minimize light loss due to contact between the waveguide and the clip. The use of TIR provides optimal efficiency and enables maximum light available and optimal direction of light 23 at first output surface 24 and second output surface 26 (best seen in FIG. 6). Light from the first output surface 24 preferably is directed distally and laterally from the waveguide to illuminate the surgical field as indicated by the arrows emanating from output surface 24. Configured for use, waveguide 14W may engage a clip such as clip 27 for securing waveguide 14W to the retractor blade connections such as clip socket 21. The clip also allows a light input cable (not illustrated) to be releasably coupled with the light input 22, and the clip also maintains an air gap around the cylindrical or round portion of the input 22 to maximum light transmission efficiency. One or more shields such as light shield 28 may also be included in waveguide assembly 14. The shield may be coupled with the clip 27 to prevent direct contact with the waveguide, and the shield helps to protect the waveguide from damage caused by other instruments in the surgical field, as well as shielding the operator from glare which may shine back into his/her eyes. FIG. 6 illustrates a side view of the waveguide assembly 14 seen in FIG. 3.

Referring now to FIG. 4, retractor assembly 12 includes retractor body 12A and retractor blade 12B. Retractor blade 12B is joined to retractor body 12A at transition zone 29 along interface 13. Transition zone 29 is configured to create drop angle 30 between blade axis 32 and retractor axis 34. Drop angle 30 is ideally between 5 and 35 degrees although any other suitable angle may be used. For thyroid surgery, drop angle 30 is about 15 degrees. Retractor blade length 36 and retractor blade depth 37 may adopt any suitable dimensions depending on the type of surgery anticipated. For thyroid surgery, blade length of 30 to 50 mm and blade depth of 25 to 60 mm are currently preferred. Of course, any dimensions may be used, and the exemplary ranges are not intended to be limiting. The inclination angle, angle 38, of the retractor blade may adopt any suitable angle. For thyroid surgery, blade inclination angle 38 of 90 degrees is currently preferred.

Retractor blade 12B has a proximal end 40 which is secured to retractor body 12A at interface 13. Distal end 42 of the retractor blade is configured for optimal utility in minimally invasive surgery. Retractor blade 12B is generally narrow along depth 37. In minimally invasive procedures it becomes important to enable tools to perform more than one function to save time and minimize movements of the surgical team. Distal end 42 is configured with a trapezoidal tip 43. In the procedure outlined below and in other procedures, an illuminated soft tissue retractor such as retractor 10 may be used for blunt dissection as well as tissue retraction. Around delicate structures it is necessary to control the amount of force applied to the tissues being dissected and extending tip width 44 expands the area of contact with the tissue being retracted and lessens the force per unit area applied to the tissue being retracted.

Figure 5:
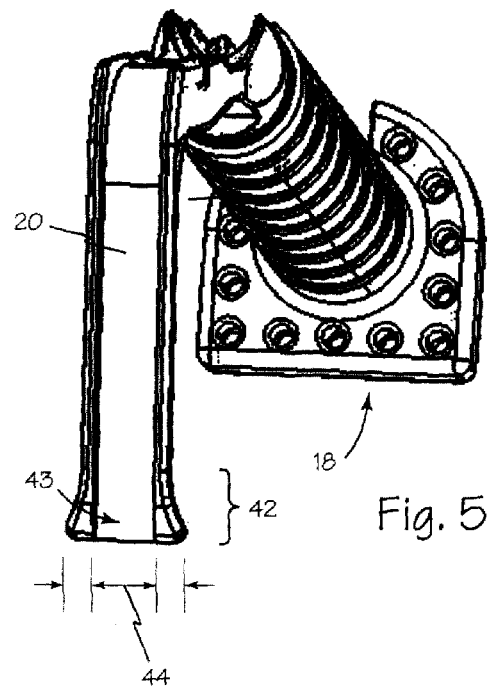
FIG. 5 is an end view of the illuminated soft tissue retractor of FIG. 1.

Retractor body 12A may also include a source of illumination such as light 46 and a portable source of energy such batteries 47 to generate illumination. FIG. 5 illustrates a front perspective view of the retractor in FIG. 4.

Illuminated soft tissue retractor 10 may be used to perform many different minimally invasive and open surgical procedures. The following example of a thyroid procedure is by way of example and is not limiting. In practice, the illuminated soft tissue retractor is used to perform a minimally invasive thyroidectomy as described below.

FIG. 7 illustrates an illuminated retractor such as the embodiment described in FIGS. 1-6 above used in a thyroid procedure. The retractor 12 is inserted into an incision I and is used to retract tissue T as described in greater detail below. This creates space for the surgeon to work and also allows surgical instruments S to be inserted into the surgical field such as an electrocautery device.

The patient is placed in the supine position. Arms padded and tucked at the patient's side. A shoulder roll is placed to extend the neck and a foam donut placed to provide head support. A pillow is placed under the patient's knee and thigh high sequential hose applied. The head of the O.R. table is raised about 10 degrees and the foot lowered 10 degrees. The patient is then prepped and draped. Drapes are placed allowing access from the suprasternal notch to the chin and laterally to the margins of the sternocleidomastoid muscles.

After draping the cricoid cartilage is located by palpation. A skin marker is used to mark the incision no more than 1 cm below the cricoid cartilage and 3-4 cm long. If the incision is made lower than 1 cm the thyroid superior poles will be more difficult to dissect. The incision is made with a #15 blade through the skin and underlying platysma muscle. Double prong skin hooks are used to retract and lift the superior skin flap. A Kelly clamp is used to dissect the subplatysma plane. The inferior platysma plane is dissected in the same fashion. Grasping the proximal projection, the illuminated thyroid retractor is now used to retract the superior skin flap and illuminate the surgical site. The connective tissue between the strap muscles may be readily identified due to the improved illumination in the surgical site. Dissection is performed through the connective tissue with a Kelly clamp and electrocautery. The strap muscles are dissected both superiorly and inferiorly. Blunt dissection is utilized along with traction-counter traction to mobilize the strap muscles from the thyroid. A peanut sponge is used for blunt dissection. Similarly, the distal end of the illuminated soft-tissue retractor may be used for blunt dissection with improved visualization of adjacent structures owing to the illumination from the TIR waveguide. The blade of the illuminated thyroid retractor is placed under the strap muscles and the proximal projection is pulled laterally to provide the necessary counter traction.

The proximal projection provides a suitable location for application of counter traction without requiring the fatiguing tension that must often be applied to conventional retractors. At this point the overhead surgical lights do not provide adequate light. The illuminated soft tissue retractor provides the light necessary to continue the procedure in the surgical cavity. Careful blunt dissection is continued with counter traction to sweep the adherent connective tissue from the thyroid lobe. This dissection is done medially to far lateral thus mobilizing the thyroid from the adjacent structures including the carotid artery.

Dissection of the thyroid superior pole is now performed with a peanut sponge and counter traction with the illuminated thyroid retractor. Once the connective tissue is dissected the thyroid lobe is retracted inferiorly and medially. The space between the thyroid gland and cricothyroid muscles is identified. A Kelly clamp and peanut sponge is used to free the thyroid gland from the cricothyroid muscle. A Babcock clamp is placed on the gland to aid retraction and place tension on the superior pole. A Kelly clamp is used to identify and dissect the superior pole vessels. The superior parathyroid gland is also identified and dissected at this time. Counter traction and illumination is maintained with the illuminated thyroid retractor while the superior poles vessels are ligated.

Once the superior pole vessels are ligated the thyroid lobe is reflected medially and superiorly. The illuminated thyroid retractor is repositioned laterally to expose the lateral and inferior structures of the thyroid gland. Peanut sponges are used to dissect the remaining connective tissue. A Mosquito clamp is used to dissect and identify the inferior parathyroid gland, thyroid vessels, and the recurrent laryngeal nerve. Meticulous dissection is required to avoid injury to the recurrent laryngeal nerve. Remaining thyroid vessels are ligated. The connective tissue between the thyroid gland and trachea are dissected with a Mosquito clamp and peanut sponges. The dissection is continued medially to the Ligament of Berry. A Mosquito clamp is used to dissect and clamp the Ligament of Berry. Sharp dissection with a #15 blade and the remaining tissue is ligated. (The same technique is then performed in the same order on the opposite lobe). Once the thyroid resection is completed hemostasis is obtained. The strap muscles are re-approximated with 3-0 absorbable suture. The dermis is closed with 5-0 absorbable suture. A 5-0 subcutiular suture is used to close the skin. Any suitable op-site dressing is used to dress the wound.

Traction-counter traction is a technique used to provide tissue dissection and visualization of the recurrent laryngeal nerves and parathyroids in a minimally invasive thyroid surgery as described above. It is critical that these structures are preserved and not injured during the thyroidectomy surgery. The traction-counter traction technique is conventionally accomplished by using a USA or Army-Navy retractor to pull the strap muscles and carotid artery sheath away from the thyroid gland and at the same time retracting the thyroid gland in the opposite direction.

In order to see into the surgical site a headlight is used. The headlight provides a unidirectional beam of light that is aimed by the surgeon. As the thyroid is dissected, the surgeon has to constantly change the position of his head, neck, and upper body in order to shine the light beam onto the different areas being dissected. Constantly having to change positions adds stress to the surgeon and in some instances he is unable to aim the light where it is needed.

Illuminated soft tissue retractor 10 has a longer and narrower retractor blade than conventional thyroid surgery retractors. The trapezoidal tip flares out providing increased surface area for retraction and dissection. The proximal projection easily engages the surgeon's hand lessening fatigue. The drop angle of 15 degrees allows the surgeon to retain his arm and shoulder in a more neutral position compared to conventional retractors. The inclusion of the TIR waveguide optimizes tissue visualization in deep surgical sites without the use of fatiguing headlamps.

In an alternate configuration, retractor assembly 12 may be formed of separable elements. Retractor blade 12B may be replaceable and may be separated from retractor body 12A at interface 13.

While the exemplary surgical method of using the illuminated retractor disclosed above is directed a thyroid surgery, this is not intended to be limiting. One of skill in the art will appreciate that the illuminated retractor disclosed herein may be used for any number of other surgical procedures, but preferably is used to retract soft tissue in head and neck procedures. Other exemplary tissues which may be retracted with the illuminated retractor described above include, but are not limited to, facial tissue during face lifts, parathyroid tissue, parotid tissue, as well as intra oral and other maxillofacial tissues.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A method of performing a minimally invasive head or neck surgery on a patient, said method comprising:
   providing an illuminated soft tissue retractor having a retractor blade, a retractor body and an illumination waveguide, wherein the retractor blade is coupled to the retractor body and the illumination waveguide is coupled to the retractor blade;
   creating a minimally invasive surgical incision in the head or neck of the patient;
   inserting the retractor blade into the incision;
   illuminating the surgical field with light extracted from the illumination waveguide, wherein the light is directed laterally and distally from the illumination waveguide to illuminate the surgical field, wherein the light is transmitted through the illumination waveguide by total internal reflection;
   counter tracting soft tissue with the retractor blade based on the weight of a proximal projection protruding from a proximal end of the retractor body while illuminating the surgical field thereby counter tracting the soft tissue without requiring squeezing of the retractor body by an operator; and
   performing the remainder of the head and neck surgery.

2. The method of claim 1, wherein performing the remainder of the head and neck surgery comprises using the soft tissue retractor to expose and dissect the patient's thyroid.

3. The method of claim 1, further comprising blunt dissection of tissue with the retractor blade.

4. The method of claim 1, wherein creating the minimally invasive surgical incision comprises making an incision no longer than 3 to 4 cm long.

5. The method of claim 1, further comprising protecting the illumination waveguide by providing a shield disposed adjacent thereto.

6. The method of claim 1, further comprising blocking glare from shining back into an operator's eyes by providing a shield disposed adjacent the illumination waveguide.

7. The method of claim 1, wherein the retractor blade comprises a proximal portion and a distal portion, and wherein the proximal portion of the retractor blade is angled downward relative to a longitudinal axis of the retractor body thereby forming a fixed drop angle therebetween, the drop angle between 5 degrees and 35 degrees, and wherein the distal portion of the retractor blade is transverse to the proximal portion of the retractor blade and transverse to the retractor body.

8. The method of claim 1, further comprising controlling the center of mass of the soft tissue retractor by coupling weights to the proximal projection.

* * * * *